(12) United States Patent
Ronto (10) Patent No.: US 9,532,857 B2
(45) Date of Patent: Jan. 3, 2017

(54) DENTAL SUCTION TUBING

(71) Applicant: David R. Ronto, Berrien Center, MI (US)

(72) Inventor: David R. Ronto, Berrien Center, MI (US)

( * ) Notice: Subject to any disclaimer, the term of this patent is extended or adjusted under 35 U.S.C. 154(b) by 0 days.

(21) Appl. No.: 13/627,521

(22) Filed: Sep. 26, 2012

(65) Prior Publication Data

US 2014/0087328 A1    Mar. 27, 2014

(51) Int. Cl.
*A61C 17/06*    (2006.01)

(52) U.S. Cl.
CPC ..... *A61C 17/043* (2013.01); *F04C 2270/0421* (2013.01)

(58) Field of Classification Search
CPC .............. A61C 17/043; A61C 17/0208; F04C 2270/0421
USPC ......................................... 433/91–96; 604/43
See application file for complete search history.

(56) References Cited

U.S. PATENT DOCUMENTS

| | | | |
|---|---|---|---|
| 3,460,255 A * | 8/1969 | Hutson ................ | A61C 17/043 433/91 |
| 4,068,664 A | 1/1978 | Sharp et al. | |
| 4,417,874 A | 11/1983 | Andersson et al. | |
| 4,487,600 A | 12/1984 | Brownlie et al. | |
| 4,695,253 A | 9/1987 | Tysse | |
| 4,767,404 A * | 8/1988 | Renton ............................ | 604/48 |
| 4,867,747 A | 9/1989 | Yarger | |
| 4,950,232 A * | 8/1990 | Ruzicka et al. ................. | 604/43 |
| 5,195,952 A * | 3/1993 | Solnit ................... | A61C 17/043 433/91 |
| 5,425,637 A | 6/1995 | Whitehouse et al. | |
| 5,441,410 A | 8/1995 | Segerdal | |
| 5,464,397 A | 11/1995 | Powers, Jr. | |
| 5,476,630 A * | 12/1995 | Orsing .......................... | 264/508 |
| 5,489,276 A | 2/1996 | Jamshidi | |
| 5,690,487 A | 11/1997 | Whitehouse et al. | |
| 5,741,134 A * | 4/1998 | Davis .............................. | 433/91 |
| 7,625,207 B2 * | 12/2009 | Hershey et al. ................. | 433/91 |
| 7,794,421 B2 | 9/2010 | Yarger | |
| 2005/0096608 A1 * | 5/2005 | Mannschedel et al. ...... | 604/264 |
| 2005/0197633 A1 * | 9/2005 | Schwartz et al. ............. | 604/264 |
| 2006/0199147 A1 | 9/2006 | Mahlmann | |
| 2007/0196783 A1 * | 8/2007 | Hasegawa ....................... | 433/91 |
| 2010/0203470 A1 | 8/2010 | Sidhu et al. | |

FOREIGN PATENT DOCUMENTS

FR    2 240 026    3/1975
FR    2 788 223 A1    7/2000

OTHER PUBLICATIONS

Henry Schein 2012 Dental Catalog, cover and p. 397 (2 pages).
Patterson Dental Supply, Inc. 2012-2013 Dental Catalog, cover and pp. 282-286 (6 pages).

(Continued)

*Primary Examiner* — Heidi M Eide
(74) *Attorney, Agent, or Firm* — Flynn, Thiel, Boutell & Tanis, P.C.

(57) ABSTRACT

A dental suction tube having a plurality of apertures in a distal portion of the tube is provided. The apertures are provided in a pattern to allow suction performance even when a portion of the distal end of the tube is abutting a portion of the mouth or other item during a dental procedure.

12 Claims, 6 Drawing Sheets

(56) References Cited

OTHER PUBLICATIONS

Partial European Search Report of the European Patent Office issued in European Application No. 13 17 7867 dated Jan. 27, 2014 (7 pages).
Search Report of European Patent Office issued in Application No. 13177867.2 dated Jun. 6, 2014 (11 pages).

* cited by examiner

DENTAL SUCTION TUBING

BACKGROUND OF THE INVENTION

The present invention generally relates to dental suction tubing, and more particularly to apparatus for the suction of fluids and solids from the mouth of a dental patient during a procedure.

In dentistry, it is very important to keep the field of view and work area of the mouth dry from water, saliva, and other materials. It is also important to keep the tongue and cheeks of the patient away from the work area.

These objectives have traditionally been accomplished by a combination of different things. A dental mirror can be used to hold the tongue, cheeks, and other structures out of the way. An air-water syringe may also be used to blow air and water into the mouth and onto the dental mirror to keep the mouth and dental mirror clean. The air-water syringe is a small metal tube that is fixed to a controller, and is rigid enough that it may hold the tongue, cheeks, or other structures out of the way, at least temporarily. Further, a dental suction tube can be used. The dental suction tube removes fluid and solid materials from the mouth to keep the mouth clean and free from encumbrances during a procedure.

However, the use of all three of these instruments together is typically not feasible and even when it is, the use of three instruments is very cumbersome. In addition, when a currently commercially available high speed suction tube is used, which has a vent hole only in the front, if it is covered by the tongue or cheek, the suction stops and thus it is rendered ineffective. The current suction devices also provide too strong of suction for a patient to expel saliva into them such that the high speed suction tube must be removed from the mouth and a slow speed saliva ejector inserted to remove excess saliva. This procedure is not only inefficient, but the slow speed saliva ejector does not allow for movement of the patient's tongue or cheeks because it is highly flexible. Accordingly, using currently commercially available instruments, dentists and dental assistants are typically using three or four devices and alternating between them to complete a procedure.

SUMMARY OF THE INVENTION

One embodiment of the present invention is a dental suction apparatus comprising an elongated substantially tubular member having an outer surface, an inner surface, a proximal portion, and a distal portion. The proximal portion defines a first longitudinal axis. The distal portion extends from the proximal portion and defines a second longitudinal axis. The first longitudinal axis is at an angle of between 150° and 180° with respect to the second longitudinal axis. A plurality of apertures are disposed helically in at least a portion of the distal portion, and each aperture extends from an outer surface to an inner surface of the substantially tubular member.

Another embodiment of the present invention is a dental suction tube comprising a proximal portion having a substantially hollow interior for the allowance of movement of material therethrough due to suction, and a distal portion connected to and extending distally from the proximal portion. The distal portion has a substantially hollow interior for the allowance of movement of material therethrough due to suction. The distal portion defines a distal end having an opening. A plurality of apertures are located in the distal portion, wherein the ratio of the total cross sectional area of the apertures to the cross sectional area of the distal end opening is in the range of about 40% to about 70%.

Yet another embodiment of the present invention is a dental suction tube comprising a proximal portion which is substantially tubular and has an exterior wall which defines a substantially hollow interior for the conveyance of material therethrough. The tube also includes a distal portion in fluid communication with the proximal portion and has a substantially hollow interior for the conveyance of material therethrough. The distal portion has a total longitudinal length, a distal end with an opening therein, and at least one exterior wall with at least ten apertures therein. The apertures are each spaced from another aperture a distance of between about 5% and about 15% of the total length of the distal portion.

Other advantages, objects and/or purposes of the invention will be apparent to persons familiar with constructions of this general type upon reading the following specification and inspecting the accompanying drawings.

DETAILED DESCRIPTION OF THE PREFERRED EMBODIMENT

Figure 1:
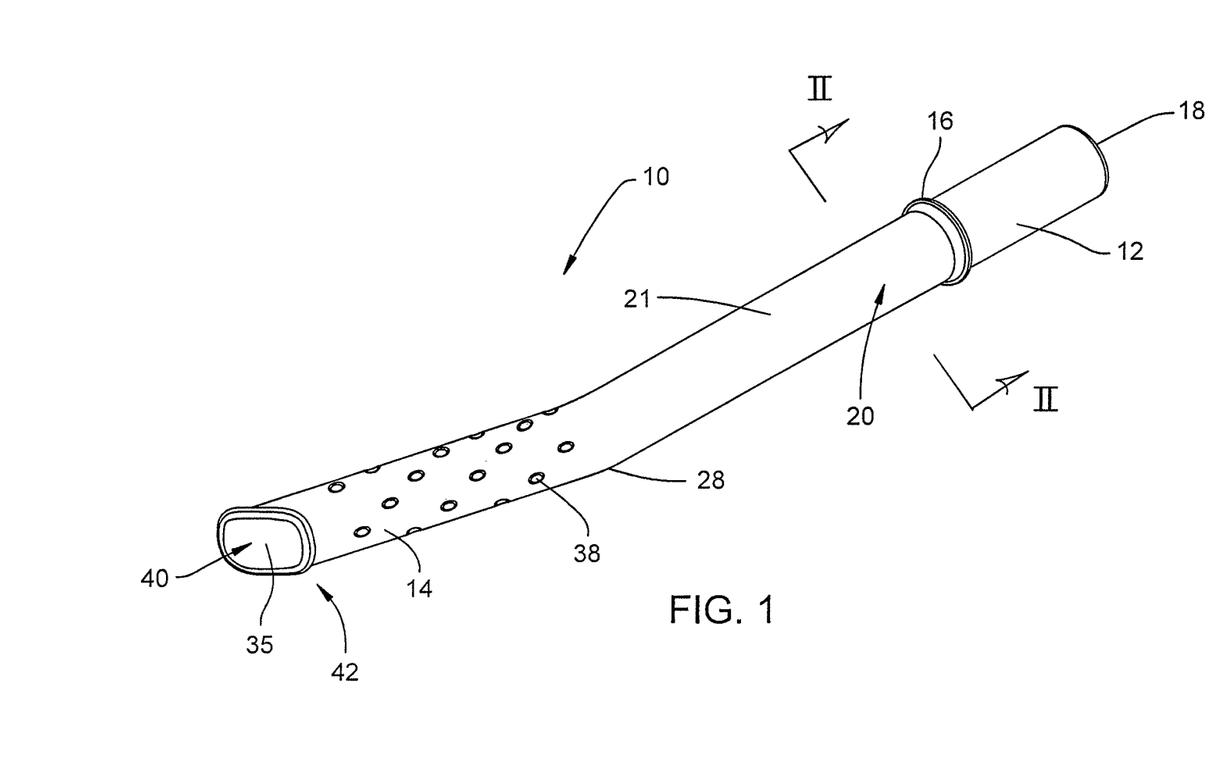
FIG. 1 is a perspective view of a dental suction tube that embodies the present invention.
Figure 2:
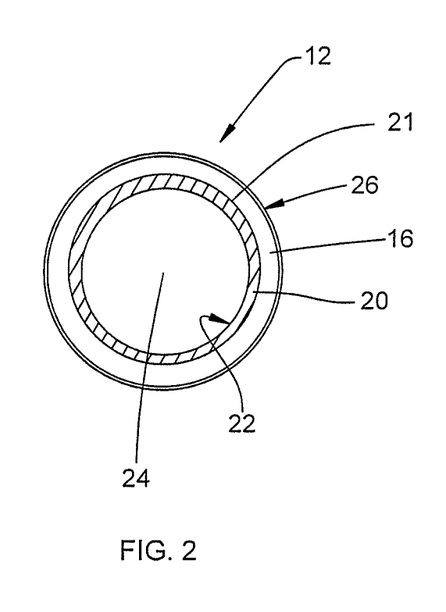
FIG. 2 is a cross-sectional view of the dental suction tube of FIG. 1, taken along line II-II.

An embodiment of a dental suction tube 10 of the present invention as shown in FIGS. 1-4. Referring specifically to FIGS. 1 and 2, the dental suction tube 10 includes a proximal portion 12, a distal portion 14, and a stop 16. The proximal portion 12 is preferably cylindrical in shape and substantially tubular in nature. The proximal portion 12 includes a proximal end 18 with an opening and an outer wall 20 having an outer surface 21 and an inner surface 22 (see FIG. 2). The proximal portion 12, and the entirety of the dental suction tube, has a substantially hollow interior 24 which allows conveyance of fluids and solids therethrough when suction is applied to the tube 10.

The stop 16 extends radially outwardly from the outer surface 21 of the proximal portion 12. The stop 16 has a generally flat surface on both its proximal side and distal side. The stop 16 preferably has a rounded or beveled outer edge 26. The stop 16 is preferably distanced from the proximal end 18 a sufficient distance to attach tube 10 to a suction device, which may be about one inch from the proximal end 18 (see FIGS. 1 and 3). The distance at which the stop 16 is located from the proximal end 18 is denoted as A in FIG. 3. The stop 16 is preferably annular, but it is contemplated that a non-annular stop with one or more members extending radially from the outer surface 21 of the proximal portion 12 may be used.

Figure 3:
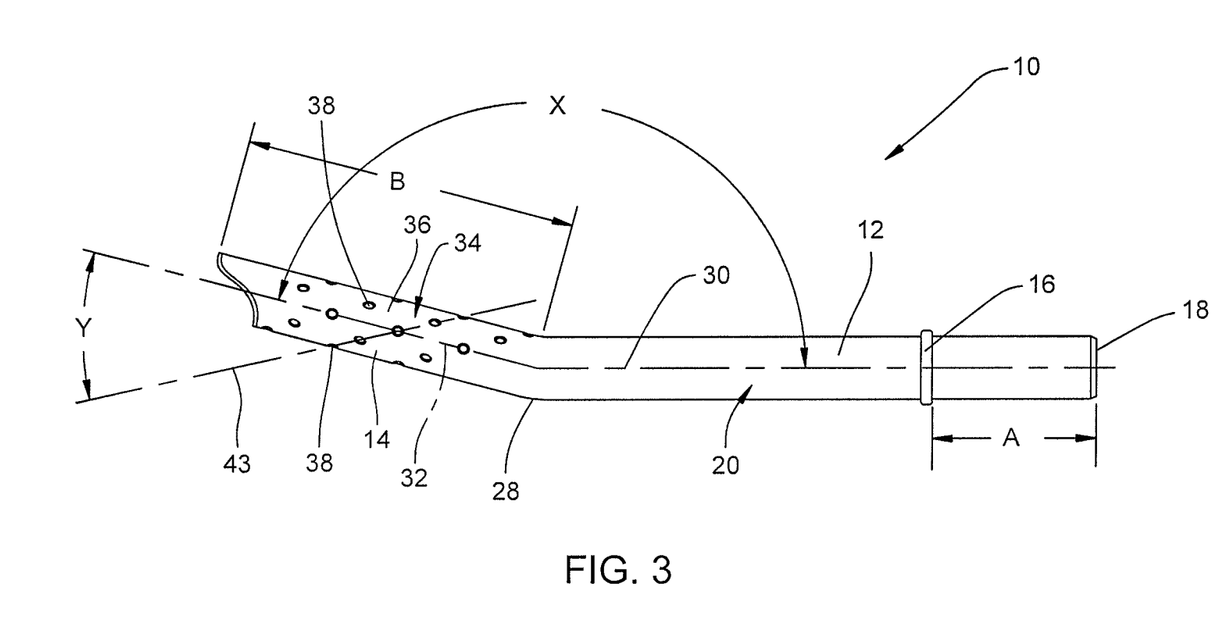
FIG. 3 is a side elevational view of the dental suction tube of FIG. 1.
Figure 4:
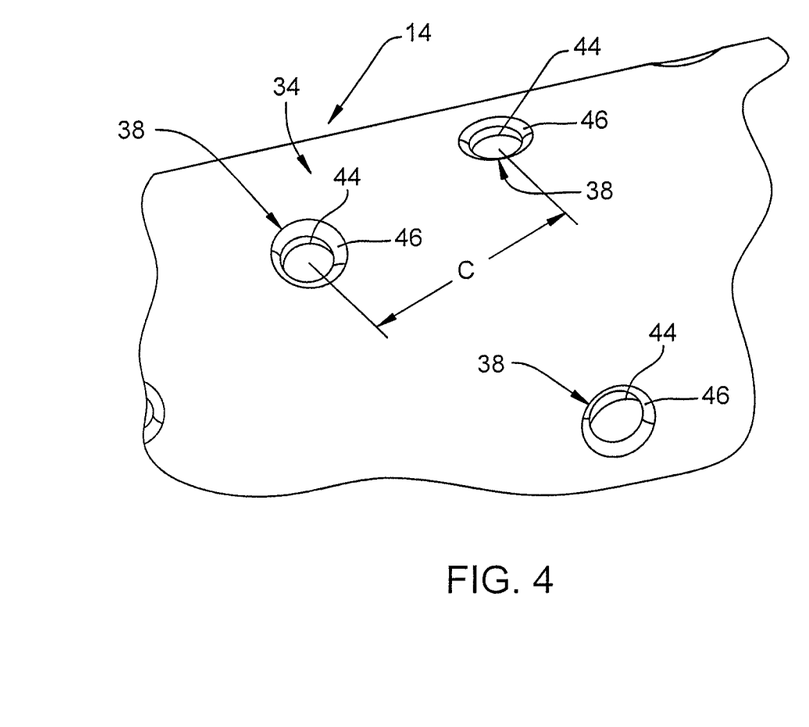
FIG. 4 is a perspective view of a portion of the distal end of the dental suction tube of FIG. 1.

As shown in FIGS. 1 and 3, tube 10 includes a bend 28 at the junction of the proximal portion 12 and the distal portion 14. The bend 28 is gradual enough to allow fluids and solids to easily pass through the distal section 14 and into and through the proximal portion 12 for removal from the procedure area. The proximal portion 12 has a first longitudinal axis 30, and the distal portion has a second longitudinal axis 32 (see FIG. 3). The angle between the first longitudinal axis 30 and the second longitudinal axis 32 is denoted by the letter X in FIG. 3. X is preferably between about 150° and about 180°, more preferably between about 160° and about 170°, and most preferably about 165°. Such an angle assists the user both in the movement or holding of potential obstructions, and in the suction of material from the work area.

The distal portion 14 of the tube 10 is formed of at least one wall 34 which is connected to wall 20 of the proximal portion 12. Thus, the distal portion 14 is in fluid communication with the proximal portion 12. Distal portion 14 preferably has a distal opening 35 and an overall length denoted as B in FIG. 3.

The wall 34 has an outer surface 36 that has a plurality of apertures 38 therein, each of which extend from the outer surface 36, through wall 34, to an interior 40 of the distal portion 14. The apertures 38 generally extend longitudinally from the bend 28 to a distal end 42 of the tube 10. Preferably, the distal portion 14 contains at least 10 apertures, more preferably more than 20 apertures, even more preferably more than 25 apertures, and most preferably about 30 apertures. However, it is contemplated that fewer than 10 apertures may be used. The apertures 38 are preferably spaced from each other a distance of at least about 5% to about 15% of the total distal portion length B.

Also, preferably, the apertures are spaced circumferentially and longitudinally (with respect to longitudinal axis 32) such that they are substantially evenly spaced over the distal portion 14. More preferably, the apertures 38 extend longitudinally in a helical fashion extending along distal portion 14 about longitudinal axis (see FIGS. 1 and 3). The helix of apertures 38 extends along an imaginary helical line designated as part number 43 in FIG. 3. The angle between line 43 and longitudinal axis 32 is denoted by the letter Y in FIG. 3. Y is preferably between about 20° and about 35°, more preferably between about 25° and about 30°, and most preferably about 27.5°.

It is preferable that each aperture 38 have the same size as the other apertures, although that aspect is not critical. The apertures 38 are preferably generally cylindrical in shape, that is, having a circular perimeter (see FIG. 4). It is more preferable that each aperture 38 include a cylindrical portion 44 which extends radially outwardly from the interior 40, and a beveled or chamfered portion 46 which extends from the outer surface 36 of the distal portion 14 inwardly radially. It is preferred that the chamfered portion 46 of each hole is rounded to provide a smooth surface and interface with the cylindrical portion 44. It is also preferred that the size of the chamfered portion in the direction of the longitudinal axis 32 is between 15% and 25%, and more preferably 20% of the diametrical distance of the aperture 38. The total cross-sectional area of all of the apertures is preferably in the range of about 40% to about 70% of the cross-sectional area of the distal opening 35 more preferably in the range of about 50% to about 60%, and most preferably about 55%.

Figure 5:
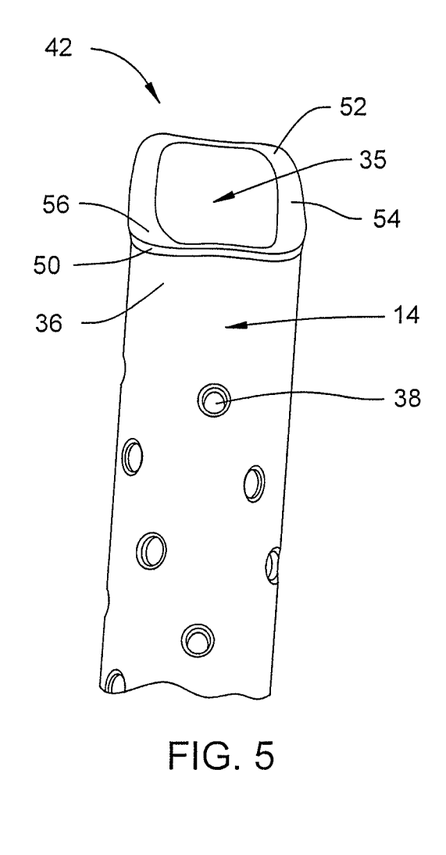
FIG. 5 is a partial bottom elevational perspective view of the distal end of the dental suction tube of FIG. 1.
Figure 6:
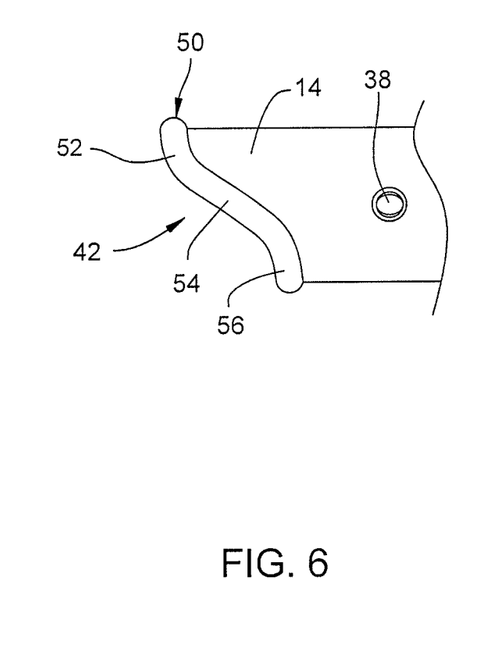
FIG. 6 is a partial side elevational view of the distal end of the dental suction tube at FIG. 1.

As shown in FIGS. 5 and 6, the distal end 42 of the tube 10 has a lip 50 surrounding the distal opening 35. The lip 50 is preferably rounded smooth so as not to injure the inside of the mouth, and extends radially outwardly from the outer surface 36 of the distal portion 14. The lip 50 preferably extends about the entire outer perimeter of the distal opening 35.

The majority of the distal opening 35 is at an angle with respect to longitudinal axis 32 which is not 90° (i.e. not perpendicular to the longitudinal axis 32). The distal end of the lip 50 has a first portion 52 which is disposed at an angle of between 80° and 90° with respect to longitudinal axis 32, a second portion 54 which is disposed at an angle of between 30° and 50° with respect to longitudinal axis 32, and a third portion 56 which is disposed at an angle of between 80° and 90° with respect to longitudinal axis 32.

The dental tube 10 is preferably made in one piece and is made of a workable rigid thermoplastic such as high density polyethylene. It is contemplated that other materials, including non-thermoplastics may be used.

The dental tube 10 gives the advantage of providing adequate suction performance during dental procedures even if a portion of the tube is blocked by a portion of the mouth or other item. The dental tube 10 is ergonomically pleasing and quiet when used due to the shape of the apertures.

Although particular preferred embodiments of the invention have been disclosed in detail for illustrative purposes, it will be recognized that variations or modifications of the disclosed apparatus, including the rearrangement of parts, lie within the scope of the present invention.

What is claimed is:

1. A dental suction tube comprising:
   a proximal portion having a substantially hollow interior for the allowance of movement of material therethrough due to suction, the proximal portion configured for attachment to a suction source;
   a substantially straight distal portion having a distal portion longitudinal axis and being connected to and extending distally from the proximal portion and having a substantially hollow interior for the allowance of movement of material therethrough due to suction, the distal portion defining a distal end having an opening, the proximal portion and the distal portion together defining the entire length of the dental suction tube;
   an outer wall extending along the entire length of the dental suction tube and having a bend at a junction of the proximal portion and the distal portion; and
   a plurality of apertures extending through the outer wall of the distal portion, the plurality of apertures being disposed along an imaginary helical line which is at an angle of between 25° and 30° with respect to the distal portion longitudinal axis, the percentage of the total cross-sectional area of all of the apertures extending through the outer wall to the cross-sectional area of the distal end opening being in the range of about 40% to about 70%, at least a majority of the plurality of apertures being proximal to the opening of the distal end.

2. The dental suction apparatus of claim 1, wherein the opening at the distal end has an outer perimeter, a smooth lip extending radially outwardly about the entire outer perimeter.

3. The dental suction apparatus of claim 1, wherein the angle of at least a majority of the opening is not perpendicular with respect to the distal portion longitudinal axis.

4. The dental suction apparatus of claim 3, wherein the opening is defined at least in part by a lip, the lip having a first portion which extends at an angle of between 80° and 90° with respect to the longitudinal axis of the distal portion and a second portion which extends at an angle between 30° and 50° with respect to the longitudinal axis of the distal portion.

5. The dental suction apparatus of claim 1, wherein the number of apertures in the distal portion is between 20 and 30.

6. The dental suction apparatus of claim 5, wherein the number of apertures in the distal portion is between 25 and 30.

7. The dental suction tube of claim 1, wherein all of the plurality of apertures are positioned proximal to the opening of the distal end.

8. The dental suction tube of claim 1, wherein the outer wall has an outer surface and each of the plurality of apertures defines a cylindrical portion through the outer wall and has a chamfer which intersects the outer surface of the outer wall.

9. A dental suction tube comprising:
   a proximal end;
   a distal end;
   a proximal portion which is substantially tubular and having a wall, the wall defining a first substantially hollow interior for the conveyance of material therethrough, the wall of the proximal portion being free of apertures; and
   a distal portion in fluid communication with the proximal portion and having a second substantially hollow interior for the conveyance of material therethrough, the distal portion having a total longitudinal length and defining a distal portion longitudinal axis, the distal end defining a distal opening therein configured to receive materials from a dental procedure site for aspiration therethrough and to the second hollow substantially interior, the distal portion having at least one wall having an outer surface and having between ten and thirty apertures therein, the apertures being disposed along an imaginary helical line which is at an angle of between 25° and 30° with respect to the distal portion longitudinal axis, the apertures each spaced from a closest positioned aperture a distance of between about 5% and about 15% of the total length of the distal portion, at least one of the apertures defining a cylindrical portion through the wall and having a chamfer which intersects the outer surface of the wall,
   wherein the proximal portion and the distal portion are joined together at a bend and together make up the entirety of the dental suction tube.

10. The dental suction tube of claim 9, wherein the proximal end has a proximal opening therein.

11. The dental suction tube of claim 9, wherein the distal opening is larger than each of the apertures.

12. The dental suction tube of claim 9, wherein the chamfer in the longitudinal direction is between 15% and 25% of a diametrical distance of the aperture.

* * * * *